(12) United States Patent
Kirkpatrick (10) Patent No.: US 9,462,797 B2
(45) Date of Patent: Oct. 11, 2016

(54) RADIOPAQUE ELASTOMERIC HORSESHOE

(71) Applicant: Sound Horse Technologies, LLC, Unionville, PA (US)

(72) Inventor: William J. Kirkpatrick, West Chester, PA (US)

(73) Assignee: SOUND HORSE TECHNOLOGIES, LLC, Unionville, PA (US)

( * ) Notice: Subject to any disclaimer, the term of this patent is extended or adjusted under 35 U.S.C. 154(b) by 0 days.

(21) Appl. No.: 14/169,133

(22) Filed: Jan. 30, 2014

(65) Prior Publication Data

US 2015/0008004 A1 Jan. 8, 2015

Related U.S. Application Data

(63) Continuation-in-part of application No. 13/404,902, filed on Feb. 24, 2012, now abandoned.

(51) Int. Cl.
*A01L 5/00* (2006.01)
*A01L 3/00* (2006.01)
*A01L 7/02* (2006.01)

(52) U.S. Cl.
CPC .. *A01L 5/00* (2013.01); *A01L 3/00* (2013.01); *A01L 7/02* (2013.01); *A61B 90/39* (2016.02); *A61B 2090/3966* (2016.02)

(58) Field of Classification Search
CPC ............ A01L 5/00; A01L 1/00; A01L 1/02; A01L 1/04; A01L 3/00; A01L 3/02; A01L 7/02; A61B 19/54; A61B 2019/5466; A61B 90/39; A61B 2090/3966
See application file for complete search history.

(56) References Cited

U.S. PATENT DOCUMENTS

| | | | | |
|---|---|---|---|---|
| 3,913,679 A | * | 10/1975 | Bucalo | A01L 1/04 168/24 |
| 4,580,637 A | * | 4/1986 | King | A01L 1/04 168/7 |
| 5,027,904 A | * | 7/1991 | Miller | A01L 7/04 168/33 |
| 5,533,575 A | * | 7/1996 | Brown | A01L 5/00 168/28 |
| 5,548,125 A | * | 8/1996 | Sandbank | A61B 19/04 250/515.1 |
| 6,082,462 A | * | 7/2000 | Lyden | A01L 1/02 168/24 |
| 2003/0167739 A1 | * | 9/2003 | Clark | A01L 5/00 54/82 |
| 2007/0055359 A1 | * | 3/2007 | Messer | A61F 2/06 623/1.34 |
| 2008/0016841 A1 | * | 1/2008 | Llewellyn | A01L 11/00 59/61 |
| 2008/0087442 A1 | * | 4/2008 | Cherel | A01L 7/02 168/12 |
| 2009/0127801 A1 | * | 5/2009 | Heikkila | A01K 85/00 277/591 |
| 2010/0294517 A1 | * | 11/2010 | Poupard | A01L 5/00 168/12 |
| 2011/0224790 A1 | * | 9/2011 | Robinson | A61F 2/30 623/14.12 |

FOREIGN PATENT DOCUMENTS

GB     1405211 A  *  9/1975  ............... A01L 5/00

* cited by examiner

*Primary Examiner* — Kathleen Alker
(74) *Attorney, Agent, or Firm* — Axenfeld Law Group, LLC; Robert R. Axenfeld (57) ABSTRACT

A horseshoe for attaching to a horse's hoof using an adhesive, such as glue. In one example, the horseshoe includes an elastomeric body containing a wear material, which improves wear and traction performance of elastomeric shoes. In another example, the elastomeric material may include radiopaque materials to improve visibility of the shoe when x-rays are taken of a horse's hoof or leg. In some aspects, the radiopaque material may be blended with the wear material. Or if the radiopaque material exhibits abrasive/gritty qualities, the radiopaque material may also serve as the wear material.

8 Claims, 12 Drawing Sheets

RADIOPAQUE ELASTOMERIC HORSESHOE

BACKGROUND

Elastomeric horseshoes, such as plastic, urethane, and rubber-polymer shoes are commonly constructed from polyurethane, plastic, or other synthetic materials. The shoes are typically about 35% lighter than forged aluminum horseshoes, and are about 70% lighter than steel shoes. Elastomeric horseshoes also absorb more concussive shock than steel or aluminum shoes and provide better wear than forged aluminum products. Radiopaque Typically, elastomeric horseshoes are glued (i.e., adhesively bonded) directly or indirectly to a horse's hoof. Adhesive bonding is frequently used when a horse is having hoof problems that preclude the use of traditional methods, such as nail-on shoes.

SUMMARY

Described herein is a horseshoe comprised of an elastomeric material. In one aspect the horseshoe includes wear material, which increases wear and traction performance of the horseshoe.

In another aspect, the elastomeric material may include radiopaque materials to improve visibility of the shoe when x-rays are taken of a horse's hoof or leg.

In another aspect, the radiopaque material may be blended with the wear material.

In another aspect, the radiopaque material may also have grit, and wear qualities. Put differently, the wear material may also be radiopaque.

This summary is provided to introduce a selection of concepts in a simplified form that are further described below. This summary is not necessarily intended to identify key features or essential features of the claimed subject matter, nor is it necessarily intended to be used as an aid in determining the scope of the claimed subject matter.

BRIEF DESCRIPTION OF THE DRAWINGS

The detailed description is explained with reference to the accompanying figures. In the figures, the left-most digit(s) of a reference number identifies the figure in which the reference number first appears. It should be noted that the figures are not necessarily drawn to scale and are for illustration purposes only.

DETAILED DESCRIPTION

Introduction

A direct-glue method simply puts glue on the horseshoe and attaches it to the horses hoof. This means the attachment is restricted to the annular surface on the bottom of the hoof wall—a modest surface area at best restricted to the portion of the hoof wall between the inner and the outer circumference.

There are two general issues with direct-glue methods: (1) attachment strength is relatively low due to the small surface area; and (2) the heel of the hoof must be securely attached to the shoe by adding additional glue that may, when used with metal and some polymeric shoes, restrict the natural lateral movement of the hoof as it loads and unloads. Some horses do not tolerate having their heels rigidly glued, and may experience heel bruises as a result. In addition, even if the heel is glued to the shoe, there may be a failure (shoe falls off) due to the relatively low attachment strength compounded by the heel's natural tendency to want to move laterally.

Another method of gluing a horseshoe to a horse's hoof involves indirectly attaching a shoe. The indirect bonding method is accomplished by the use of a fabric cuff that is saturated with glue and placed on the outside vertical section of the hoof wall. Generally, no glue is used on the bottom of the hoof. This is a much stronger attachment for several reasons. First, the attachment mode has the adhesive (glue) operating in stronger shear direction instead of tensile with the direct-glue system. Add to that the large increase in surface area for the vertical cuff.

As an example of just attachment area, a common horseshoe size of "medium or size 1" has an approximate perimeter (heel thru toe to heel) of 15 inches. If the shoe is directly glued to the bottom of the hoof, about half the shoe width (say 0.5 inch) would be involved in the attachment strength—15 inch perimeter×0.5 inch width=7.5 square inch surface area acting in tensile. The indirect method utilizing a modest cuff up the vertical sides of the hoof around the perimeter of the same shoe delivers far more attachment area and the glue is working in shear—15 inch perimeter×1.5 inch cuff height=22.5 square inches of surface area acting in shear.

Assuming that a horse's hoof requires something other than nails for a secure attachment, there are applications that a direct glue—direct to the bottom of the hoof—method will work and many where it is less desirable than an indirect system.

For instance, for straight-line work such as a race track, the system of directly gluing on shoes is sometimes sufficient. However, introduce any jumping, cutting, and turning that tends to be typical of many of the other equestrian pursuits off the track, and the direct-glue system of attachment will frequently deliver inadequate performance.

This is not true of the indirect "glue-on" system that employs the cuff working in shear on the vertical aspect of the hoof. The cuffed system works in all equine pursuits and is advantaged in that it does not have glue on the bottom of the hoof and the heel is permitted to move naturally and laterally on the shoe heel.

Regardless of whether a shoe is directly or indirectly glued on to the horseshoe, there is a desire to use elastomeric horseshoes commonly referred to in the industry as "polymer shoes", which can generally match the shape of any steel shoe. Because polymer shoes are commonly constructed from polyurethane, plastic, or other urethane materials, the shoes are lighter (about 35% lighter than forged aluminum horseshoes), may be less expensive, and absorb more concussive shock than steel or aluminum shoes.

However, glue-on horseshoes that are made of flexible materials, such as synthetic polymers, often do not have enough rigidity to prevent the branches of the heel portion of the shoe from moving apart (i.e., laterally) when under load. That is, an elastomeric horseshoe generally does not have enough rigidity to prevent the branches of the heel portion of the shoe to move apart (i.e., laterally) when under load. This includes polymeric open-heel horseshoes with reinforced members.

As a result, a horse's heel can fall inside the heel of the horseshoe as it is flexed and moved under load. And, once the horse's heel descends inside the heel of a polymer shoe, the usefulness of the shoe in relation to the hoof is catastrophically ended.

To solve these and other problems associated with elastomeric glue-on horseshoes, described herein is an example elastomeric horseshoe that may include a resilient plate. The resilient plate may be generally flexible, and may be composed of a fiber reinforced material, or other flexible materials. The resilient plate generally extends between a heel portion of branches of the horseshoe. The plate, therefore, stabilizes the heel portion of the horseshoe by minimizing or eliminating movement the branches away from each other in a lateral direction when the heel portion of the shoe is under load.

So, in embodiments described herein, the resilient plate, when fastened or integrated between the branches of a shoe, substantially eliminates outward lateral movement of the branches, when the shoe is under load by a horse.

Additionally, in one embodiment, the resilient plate is generally planar, flexible, and flat so as to generally avoid providing support to a horse's frog when the shoe is attached to the horse's hoof.

Additional examples, and details of such horseshoes is described in greater detail below.

Reference herein to "one embodiment", "an embodiment", "an implementation" or "one implementation" "an example" or similar formulations herein, means that a particular feature, structure, operation, or characteristic described in connection with the embodiment or example, is included in at least one embodiment of the detailed description. Thus, the appearances of such phrases or formulations herein are not necessarily all referring to the same embodiment or example. Furthermore, various particular features, structures, operations, or characteristics may be combined in any suitable manner in one or more embodiments or examples.

As used herein the term "horse" refers to any hoofed animal in the equine family or others that may wear shoes that attach to their hoofs, such as a horse, a pony, a donkey, a mule, or other animals having keratinous hoof materials.

Example Elastomeric Horseshoe with Slots

Described herein is a horseshoe for attaching to a horse's hoof using an adhesive, such as glue.

Figure 1A:
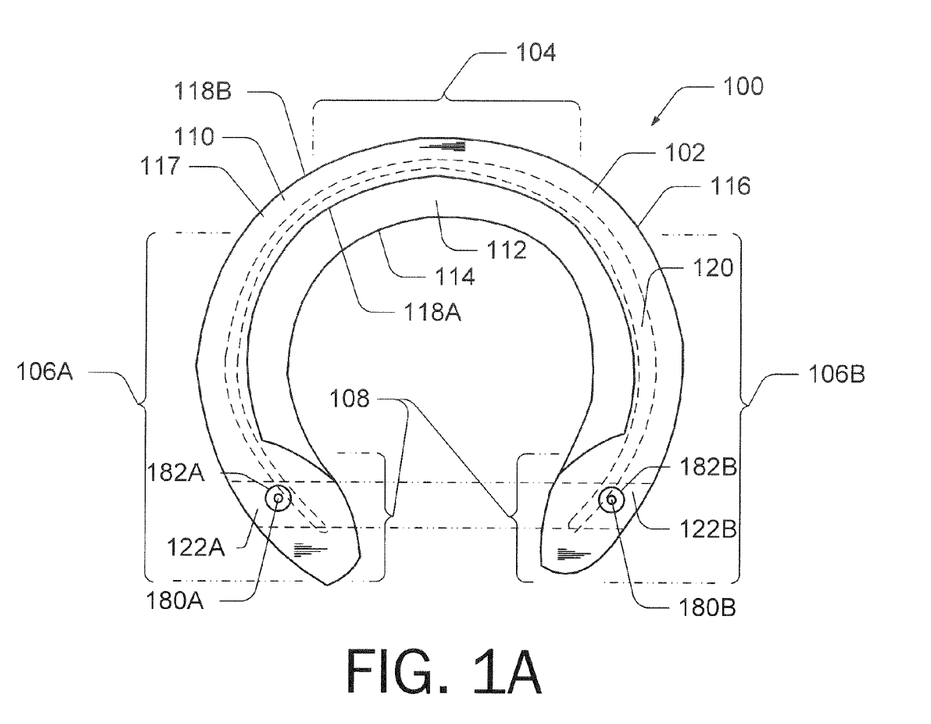
FIG. 1A shows a top view of an example glue-on horseshoe.

FIG. 1A shows a top view of an example glue-on horseshoe 100. Horseshoe 100 may include an elastomeric body 102 containing a toe portion 104, a first branch 106A, a second branch 106B, and a heel portion 108. Toe portion 104, and first and second branches 106A, 106B may also include generally inner and outer edges 114, 116, respectively, as well as generally hoof-facing surface 110 and ground-facing surfaces 150 (see, i.e., FIG. 1B). Each surface may include several levels of surfaces.

For instance, hoof-facing surface 110 may include elevated surfaces such as a rim 117. Rim 117 typically has an inner edge 118A and outer edge 118B for contacting the outer periphery of a horse's hoof wall. Hoof-facing surfacing 110 may also include a concave-relief section 112. Rim 117, hoof-facing and ground-facing surfaces 110, 150 and concave-relief sections 112 are also depicted in FIG. 2, which is an isometric view of toe portion 104 of shoe 100 shown in FIG. 1A.

Figure 2:
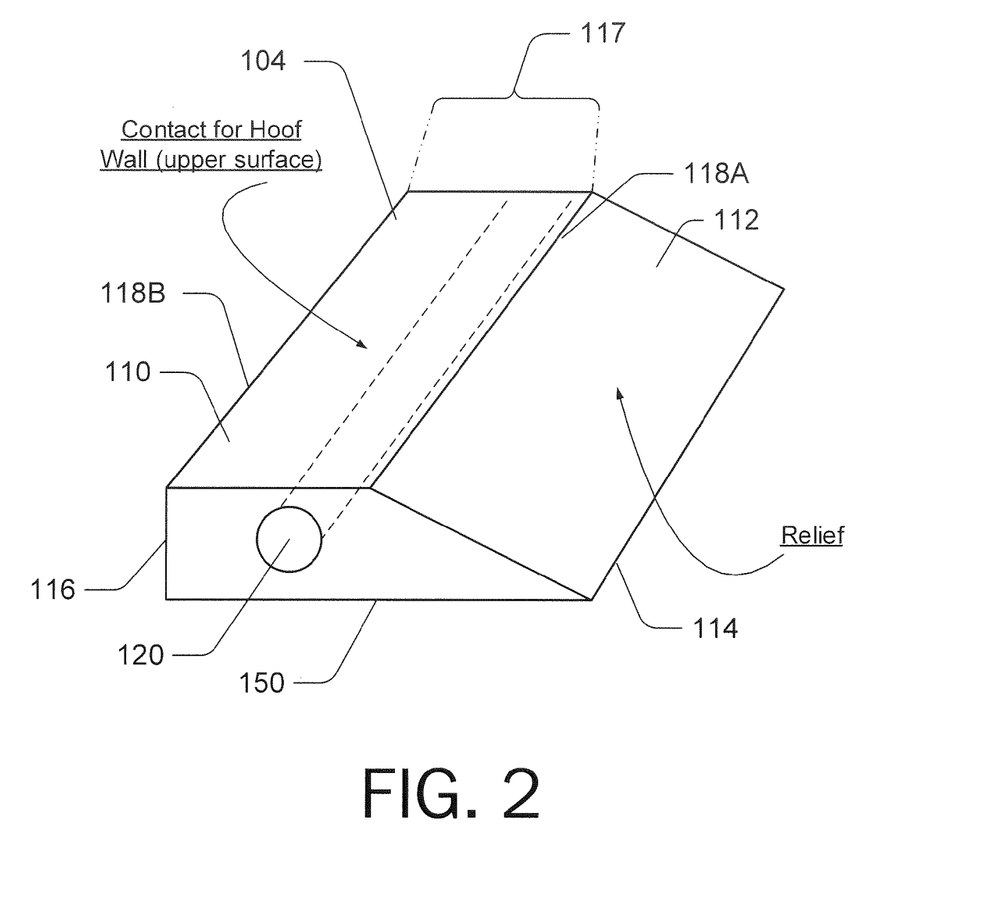
FIG. 2 is an isometric-cross-sectional view of a toe portion of an example horseshoe, such as shown in FIGS. 1A and 1B.

Referring to FIG. 2, rim 117 typically has an inner edge 118A and outer edge 118B for contacting the outer periphery of a horse's hoof. Concave-relief section 112 prevent portions of hoof-facing surface 110 from contacting the thin and sensitive sole of the hoof.

Figure 1B:
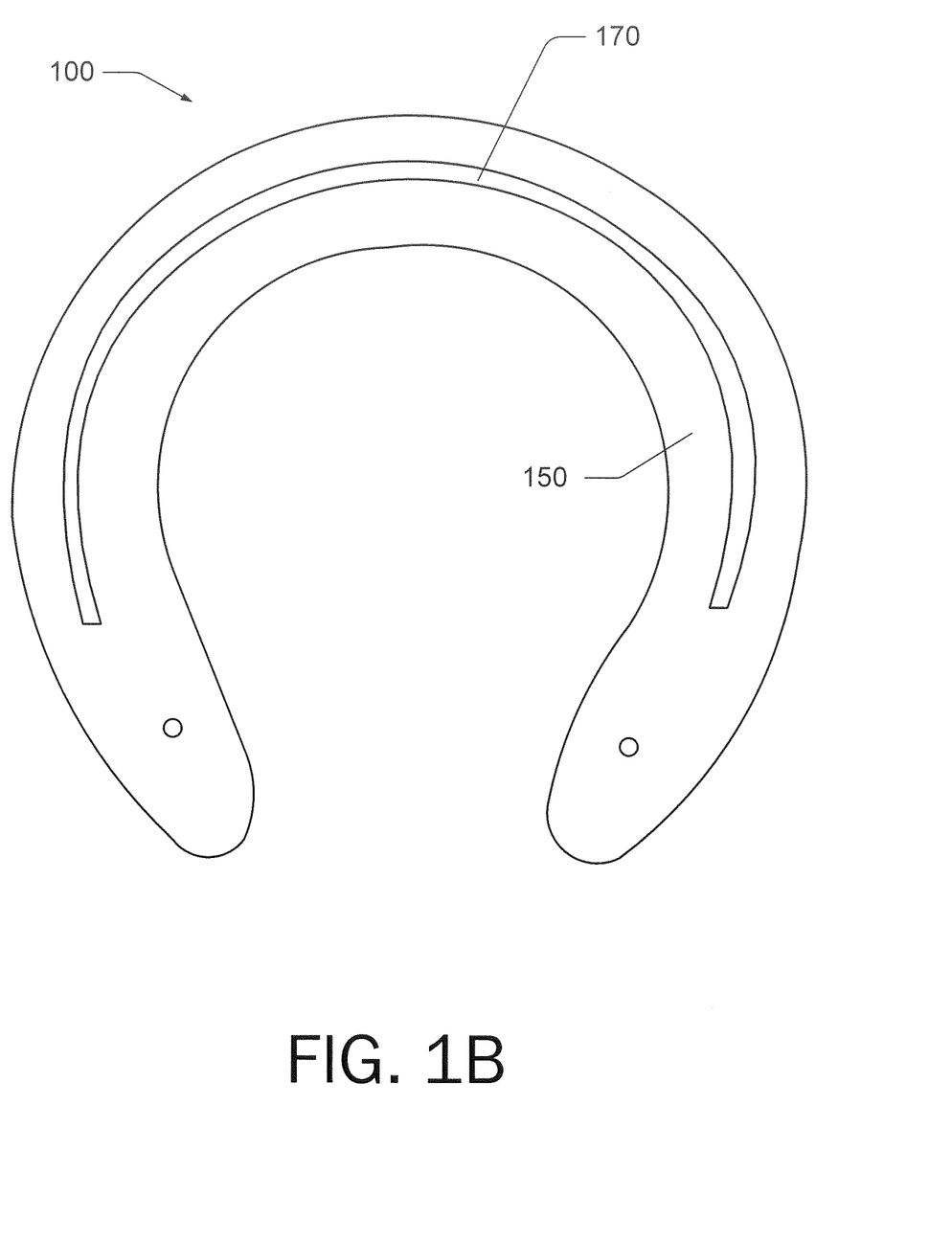
FIG. 1B shows a bottom view (i.e. the ground-facing surface) of an example glue-on horseshoe.

FIG. 1B shows a ground-surface view of the example horseshoe in FIG. 1A. As depicted in FIG. 1B, shoe 100 may include a "fullered" nail crease 170 to provide improved traction. In this embodiment, nail crease 170, combined with a narrower ground contact shape of the inner and outer rim, reduces the surface area of ground-facing surface 150, thereby increasing the shoe's unit loading, or in other words, the ability of the shoe to "dig" into the ground. Further, "nail crease" 170 tends to fill with small stones, which may also improve performance traction of the shoe.

In one embodiment, nail crease 170 is approximately ¼ inch in width, and may extend partially or fully along ground-facing surface 150 of shoe 100. As appreciated by those skilled in the art having the benefit of this disclosure, however, the size and location of a nail crease 170 may vary. Additionally, more than one nail crease or various configurations may be implemented in the bottom of ground-facing surface 150 of shoe 100.

Referring back to FIG. 1A, body 102 is generally U-shaped (open heels). However, body may include other suitable shapes, sizes, and configurations. Body 102 is generally comprised of an elastomeric material that is flexible yet rigid enough to resist full deformation under load while maintaining shape integrity, such as a stiff rubber, a polymer, a polyurethane, urethane, a composite material, or other durable, generally non-metallic, but flexible materials.

As appreciated by those skilled in the art having the benefit of this disclosure, different materials having different hardness and stiffness characteristics may be used to form different layers or portions of elastomeric body 102.

Example Braces

Example horseshoe 100 may use or incorporate one or more braces to retain a shaped position of the branches 106A, 106B after one or more braces 120 are possibly shaped by a farrier. That is, the brace(s) may be composed of any suitable material, and configuration able to bend and retain a shape of shoe 100, and therefore, resist the elastomeric propensity of body 102 to return to its original molded or cast shape after braches 106A, 106B are flexed/shaped.

As depicted in FIGS. 1 and 2, example horseshoe 100 includes an example brace 120 comprised of a unitary-bendable rod encapsulated within body 102. Brace 120 is generally cylindrically shaped, and has a general overall diameter of about ⅛th of an inch, and an overall length extending almost the entire U-shaped horseshoe 100. As appreciated by those skilled in the art with the benefit of having this disclosure, the rod may also be non-cylindrical in shape, and be of other suitable sizes and lengths depending on the type and size of horseshoe used.

Figure 3:
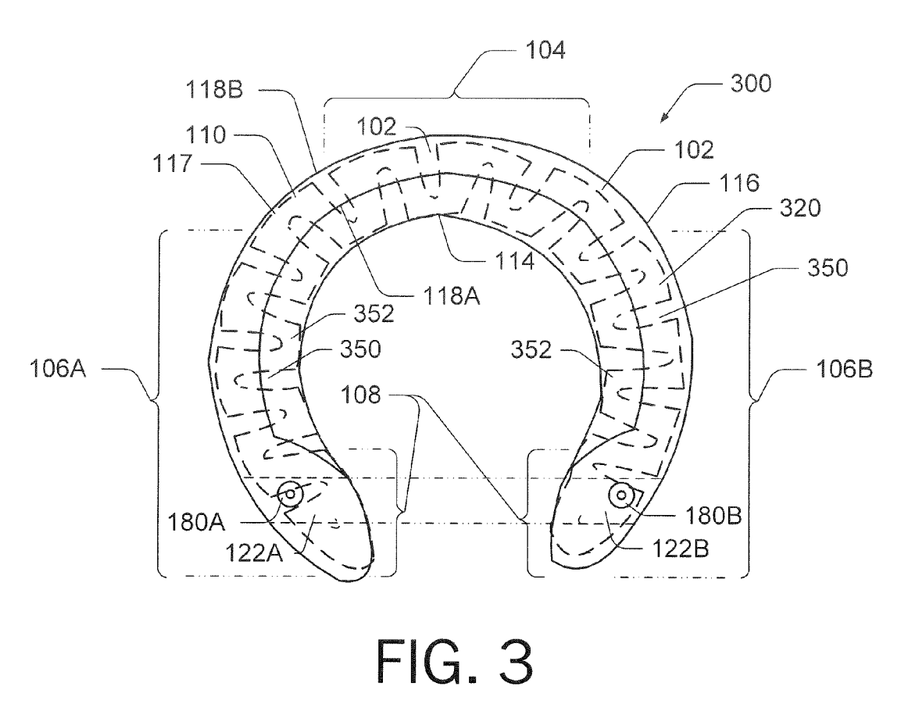
FIG. 3 shows a top view of an example horseshoe with a segmented-metallic brace encapsulated within an elastomeric body of the shoe.

Additionally, brace 120 may include other suitable shapes and sizes. For example, FIG. 3 shows a top view of a horseshoe 300 with a segmented-metallic brace 320 in lieu of a rod (such as brace 120 of FIGS. 1 and 2) encapsulated within elastomeric body 102. Example brace 320 depicted in FIG. 3 may include one or more slots 350. Separating each slot 350 is a non-slotted section 352 which is intact. This combination of slots 350 and non-slotted sections 352 forms the overall segmentation of brace 320, and provides a farrier with the ability to easily bend body 102. And, once bent into a shape selected by the farrier, the overall segmentation of brace 320 also permits brace 320 to retain most shapes selected, while resisting the propensity of elastomeric body 102 to return to its original shape after being adjusted by a farrier. Brace 320 is generally planar and has thickness of about 1/16 of inch. Brace 320 has a width measured from an inner edge 114 to an outer edge 116 of shoe 300, which may vary depending on the size of the shoe. As appreciated by those skilled in the art after having the benefit of this disclosure, brace 320 may be thicker, or thinner, and have widths that are wider or narrower.

Additionally, as appreciated by those skilled in the art having the benefit of this disclosure, a brace may include multiple components, and may be of other suitable sizes and shape. Example braces 120 and 320 shown in FIGS. 1 and 3, respectively, may be formed of a metallic material such as aluminum, titanium, steel, a combination of metallic materials, or some other suitable material(s) that may not be metallic.

Although shoes 100 and 300 show braces 120, 320 encapsulated within body 102, it is also possible for a brace to be positioned on an external surface of body 102, or partially within and out of body 102.

Example Horseshoe with No Brace

Figure 4:
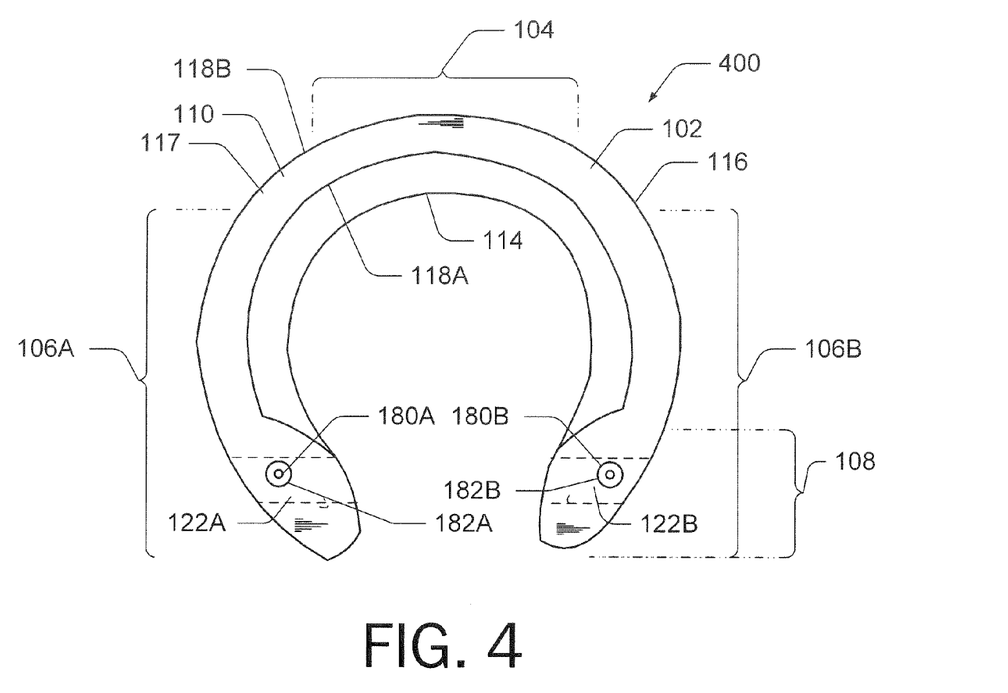
FIG. 4 shows a top of view of an example horseshoe with no brace.

Further, body 102 may include no brace. For instance, FIG. 4 shows a top of view of an example horseshoe 400 with no brace. Shoe 400 is especially suitable if the size and shape of a horse's hoof is known beforehand, and little to no adjustment in the shape of shoe 400 is required before fastening shoe 400 to a hoof.

Example Slots

Referring to FIGS. 1, 3, and 4, example horseshoes 100, 300, and 400 may also include slots 122A, 122B laterally extending through heel portion 108 of branches 106A, 106B, respectively. In the example shoes 100, 300, 400, slots 122A and 122B extend between inner edge 114 and outer edge 116 of heel portion 108 of respective branches 106A, 106B. That is, horseshoe 100 may include a first slot 122A (shown in cross section) that extends laterally through heel portion 108 of first branch 106A, and a second slot 122B (shown in cross section) that extends laterally through heel portion 108 of second branch 106B, and substantially aligns with first slot 122A.

As appreciated by those skilled in the art with the benefit of this disclosure, however, openings of slots 122A, 122B may not necessarily extend all the way through branches 106A, 106B. Rather, one or more openings of slots 122A, 122B may extend only partially through branches 106A, 106B, such as ⅓, ½, or ¾ (or other partial distances) of the way through a branch 106, when measured from inner edge 114. As depicted, the openings of each slot 122A or 122B extend perpendicularly to at least a portion of branches 106A, 106B.

Figure 5:
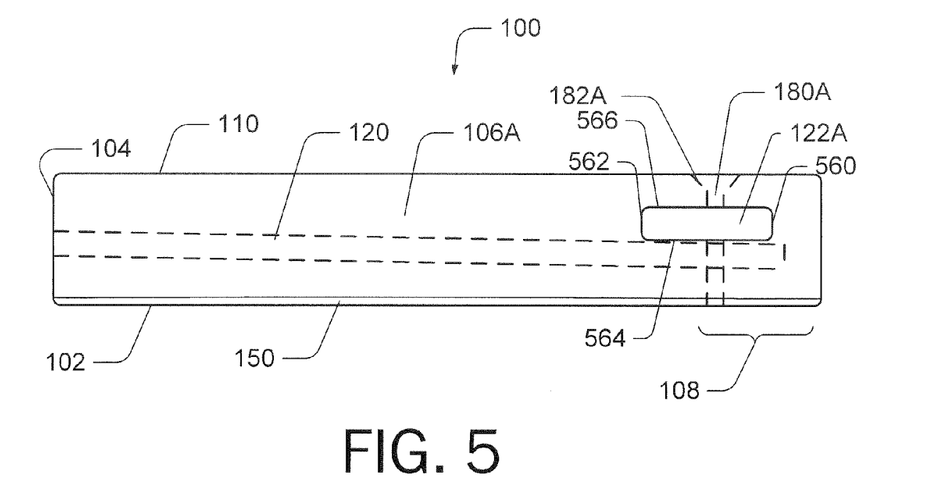
FIG. 5 is a left-side view of example horseshoes shown in FIGS. 1, 3 and 4.

FIG. 5 is a left-side view of example horseshoes 100, 300 and 400, shown in FIGS. 1, 3 and 4, respectively. As depicted in FIGS. 1, 3, 4, and 5 slots 122A, 122B, again, generally align with each other, and are positioned generally parallel to, and between hoof-facing surface 110 and ground-facing surface 150. As depicted in FIG. 5, slots 122A, 122B (not visible in FIG. 5) are positioned substantially midway between a hoof-facing surface 110 and ground-facing surface 150. In other examples, however, slots 122 may be positioned closer to either hoof-facing surface or ground-facing surface 112.

Example slot 122A of FIG. 5 is generally about ¾ of an inch in length when measured from inner walls 560 and 562 of slot 122A, and has an internal height of about ⅛ of an inch when measured between inner wall 564 and inner wall 566. Also, inner walls 564, 566 of slot 122A is about ¼ of inch away from ground-facing surface 150 the highest surface of hoof-face surface 110 (located approximately midway between the ground surface, and the hoof surface of the shoe).

As appreciated by those skilled in the art having the benefit of this disclosure, other suitable dimensions and locations of slots 122 are possible. Additionally, it is possible for each slot 122 to be asymmetrical, and not necessarily align in height, length and position with each other.

As also depicted in the side of FIG. 5, a brace (such as example braces 120 or 320) may pass underneath one or more portions of slots 122. Alternatively, each brace may not extend to slots 122, or be positioned over one or more portions of slots 122.

Example Fastening Holes Aligned with Slots

Also, referring to FIGS. 1, 3, 4, and 5, example shoes 100, 300 may also include holes 180A, 180B each aligned with a respective slot 122A, 122B. In one example, each hole 180 is a tap hole, configured to receive a fastening device, such as a screw.

Each hole 180 may include a wider-recessed section 182A, 182B to receive a the head of a fastening device, so that when the fastening device is fully inserted into hole 180, the head of the fastening device is flush with or contained fully within hoof-facing surface 110 (a/k/a "countersunk"). Alternatively, the direction of wider-recessed sections 182A, 182B of holes 180A, 180B, may be reversed (not shown), so that wider-recessed sections 182 are flush with or contained fully within ground-facing surface 150.

Although, each branch 106A, 106B shows a single hole 180, as appreciated by those skilled in the art having the benefit of this disclosure, additional holes may be included in branches 106A, 106B to receive one or more suitable fastening devices.

Thus, example holes 180A, 180B may pass at least partially through at least one of hoof-facing surface 110, ground-facing surface 150, or both. Additionally, holes 180A, 180B, are aligned with slots 122A, 122B, respectively. Holes 180 may also include varying widths (such as wider-recessed sections 182) and depths.

Example Resilient Plates

Figure 6:
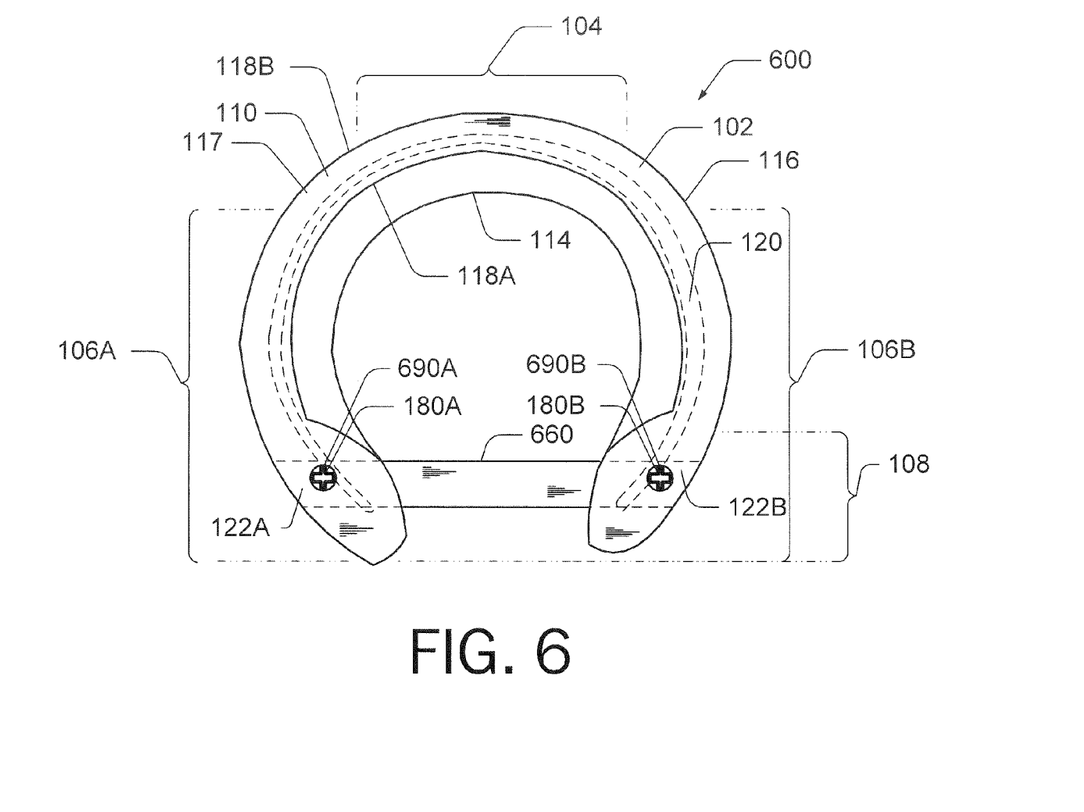
FIG. 6 shows a top view of an example horseshoe, which includes a resilient plate extending between slots of the branches of a heel portion of the shoe.

FIG. 6 shows a top view of an example horseshoe 600, which includes a resilient plate 660 extending between first and second slots 122A, 122B. In this example, plate 660 is fastened to slots 122A, 122B via a fastening device inserted through holes 180A, 180B, and which also passes through plate 660 in slots 122A, 122B. That is, screws 690A, 690B pass through plate 660 via holes 180A, 180B, and secure plate 660 to branches 106A, 106B. Screws 690 may be a countersunk screw with interrupted threads (not shown) to ensure a strong grip to polymer materials, such as body 102 of branches 106A, 106B.

As would be readily appreciated by those skilled in the art, other fastening device may be used in place of, or with screws 690, such as clips, snaps, bolt and nut systems, rivets, and so forth. It is also possible for a suitable fastening device, such as a clip, not to pass through plate 660.

As depicted in FIG. 6, example plate 660 is substantially perpendicular to at least a portion of the first and second branches 106A, 106B. Further, example plate 660 is generally commensurate in size and shape than the inner portion of each slot 122A, 122B, but with a slightly smaller tolerance than the inner portion of each slot. In other examples, plate 660 may be other sizes or shapes providing a tighter or looser fit with slots 122. The fit tolerances are critical to permitting the single fastener to generate adequate holding strength to secure the connecting plate for the entire shoeing interval.

In this example plate 660 does not have tap holes. So screws 690 may be used to drill through plate 660 when being installed in slots 122. In other examples, plate 660 may include tap holes configured to align with holes 180 of slots 122.

When under load of a horse's heel, unstabilized branches 106A and 106B may flex in a lateral direction away from each other without plate 660, and a horse's hoof can drop inside heel portion 108 of a polymer horseshoe. So, when an example plate 660 is secured between braches 106A and 106B, plate 660 substantially prevents branches 106A and 106B from moving away from each other laterally, such as in a horizontal plane.

Thus, when installed in shoe 600, plate 660 is configured to hold heel portion 108 of branches 106A and 106B, in a stable, relative fixed position with respect to each other when under load. Specifically, plate 660 secures against lateral movement of branches 106A and 106B away from each other, so that the distance between the two branches does not expand laterally in the same plane. Plate 660, however, does not necessarily prevent branches 106A and 106B from moving in vertical plane, such as flexing up and down.

Figure 7:
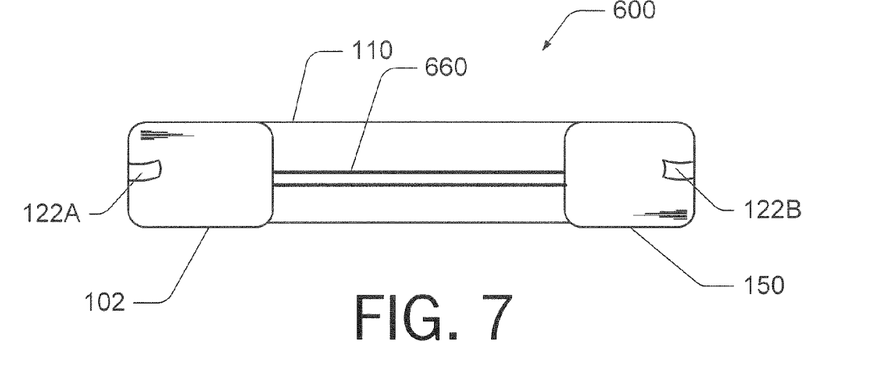
FIG. 7 shows a back view of a shoe from with an example plate in a neutral position.

Example plate 660 is flexible and resilient. For instance, FIG. 7 shows a back-view of shoe 600. As depicted, plate 660 is in a neutral position when a horse is standing in equilibrium, and the frog of a horse's hoof does not typically touch the ground. In this position, plate 660 may not touch or may just abut the frog. So, plate 660 is not supporting the horses weight and prevents outward-lateral movement of heel potion 108 of branches 106, to prevent the horse's hoof from dropping off the shoe and onto the ground. Heel portion 108 of branches 106 are permitted to move vertically (up & down) while the horse's heel can move laterally by sliding on the hoof-facing surface (specifically heel portion 108) of a shoe.

Figure 8:
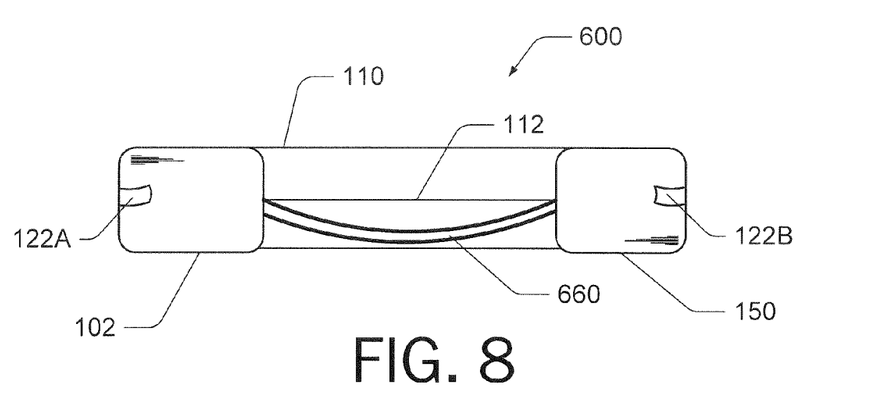
FIG. 8 shows a back view the same horseshoe shown in FIG. 7, but with the example plate flexing downward under full load of the frog portion of a horse's hoof.

On the other hand. FIG. 8 shows a back view of shoe 600. Here plate 660 is flexed and touching the ground, such as when the frog of a hoof descends under load striking the ground. As depicted in FIGS. 7 and 8, example plate 660 is not configured to support the frog. Rather, plate 660 is resilient and flexible allowing the frog to behave naturally by offering no vertical support to the frog.

Figure 9:
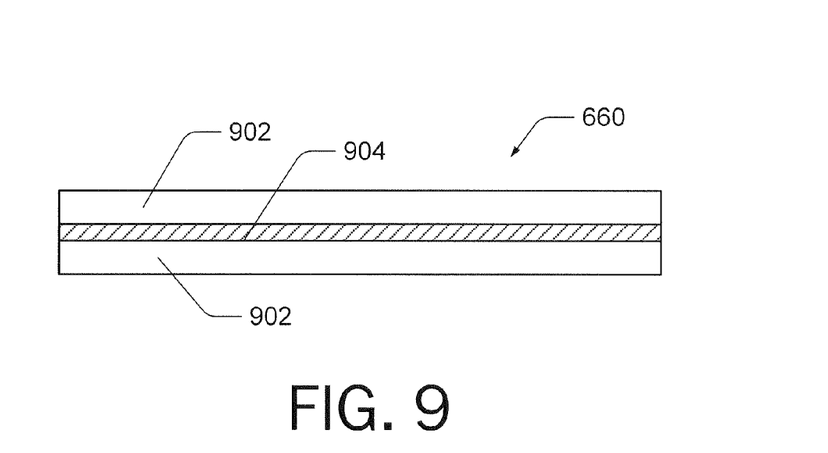
FIG. 9 shows a side-cross-sectional view of an example plate.

FIG. 9 shows a side-cross-sectional view of an example plate, such as plate 660. As depicted in FIG. 9, plate 660 is planar, and includes one or more layers of fabric or other material 904 encapsulated at least partially in a flexible-polymeric material 902. In one example, material 904 is a woven-fabric, such as a polymeric fabric. In other examples, woven-fabric material 904 is a carbon-fiber fabric. Material 904 may be a single-ply or multi-ply layers. Each layer of material 904 may also be directionally braided.

For example, material 904 may constructed of roughly equal quantities of polyester and Vectran™ (a liquid crystal polymer or polyester) graded in a two-ply configuration. Polyester is used to deliver high bonding strength with adhesive, is flexible, and works well in wet environments without structural weakening. However, other suitable materials may be selected in place of polyester, which provide similar attributes as polyester as would be appreciated by those skilled with the benefit of having this disclosure, such as nylon, and other synthetic or non-synthetic materials.

As appreciated by those skilled in the art having the benefit of this disclosure, more or less layers of material may be used to construct a flexible and resilient plate 660. Additionally, different types of materials may be selected to construct plate 660 including composite materials.

For instance, plate 660 may include a metallic material, such as aluminum or steel (not shown). Additionally, plate 660 may include encapsulating materials, such as a polymeric material. Alternatively, plate 660 may not be encapsulated or be constructed of a single unitary material. The system will allow the farrier or veterinarian to choose whether to use the supplied flexible element or a rigid metal material to best satisfy the therapeutic needs of the equine patient.

Figure 10:
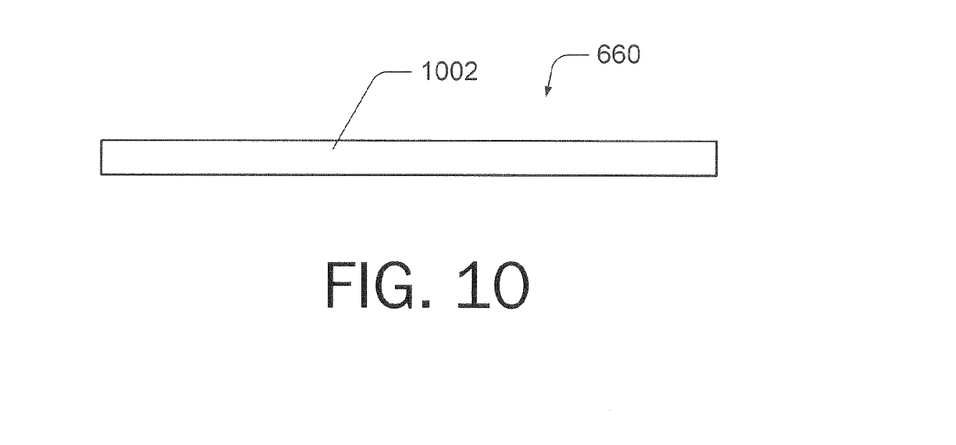
FIG. 10 shows a side view of an example plate constructed of a suitable material(s), which are flexible and resilient.

For instance, FIG. 10 shows a side view of another example plate 660 constructed of a flexible and resilient unitary material. Suitable material may include rubber ABS, polyurethane, or other "plastic" materials with performance properties suitable for the therapeutic or competitive demands.

Figure 11:
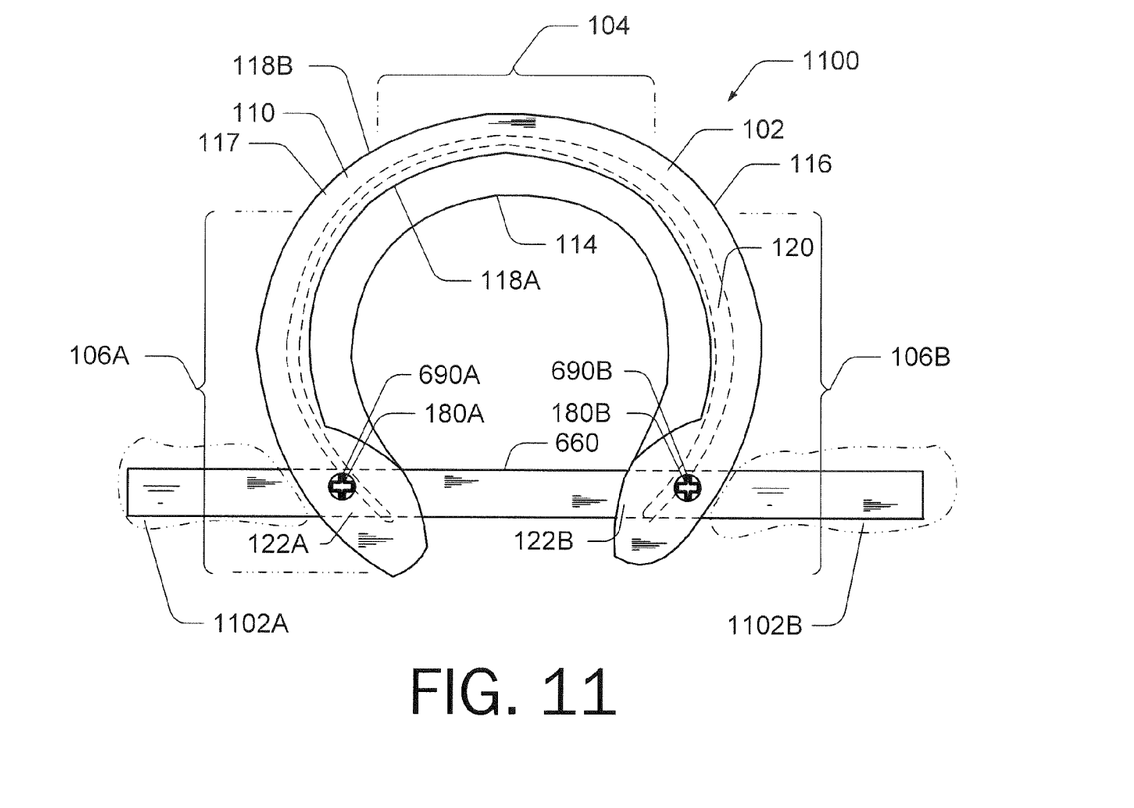
FIG. 11 shows a top view of an example horseshoe with a plate secured therein, before excess material of the plate is trimmed off such as when being installed in a horseshoe by a farrier.

FIG. 11 shows a top view of an example horseshoe 1100 with a plate 660 secured therein, before excess material is trimmed off, so that the length of the plate matches the width of a heel portion 108 of the horseshoe.

As depicted in FIG. 11, the excess material is located at distal ends 1102A, 1102B of plate 660. That is, the length of plate 660 extends beyond outer edge 116 of slots 122A, 122B. This excess material may be cut away so that distal ends 1102A, 1102B of plate 660 become flush with outer edge 116 of slots 122A, 122B. Typically, the excess material is cut away after plate 660 is installed and secured in place by fasteners, such as screws 690A, 690B.

Figure 12:
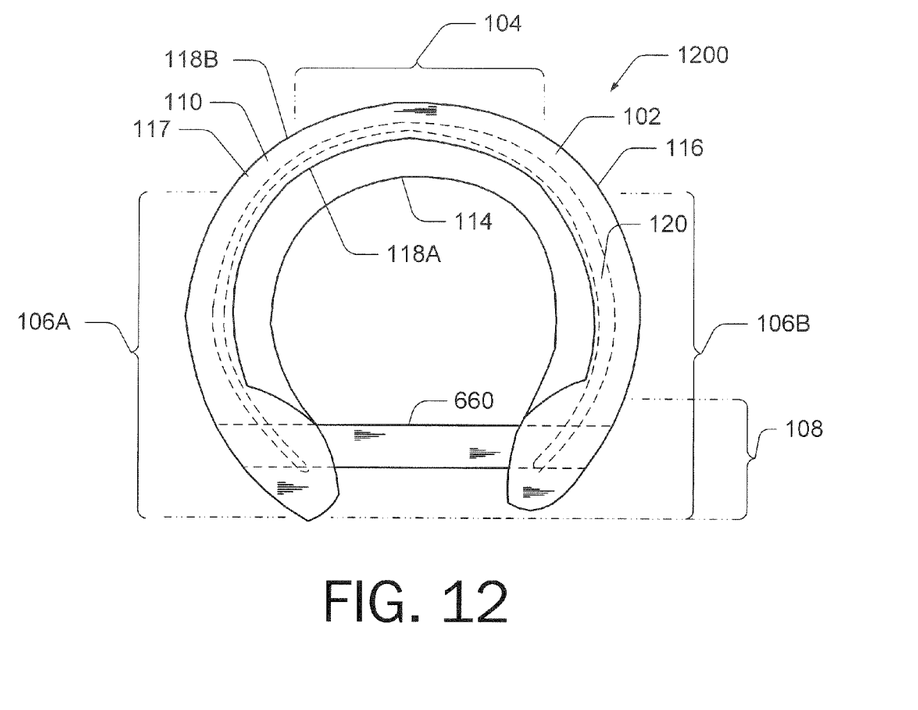
FIG. 12 shows a top view of an example horseshoe with a plate that is cast into the shoe at the time of manufacture.

FIG. 12 shows a top view of an example horseshoe 1200 with a plate 660 that is cast into the shoe at the time of manufacture. In this example, because plate 660 is an integral part of body 102, additional fastening devices and slots are not required to secure plate 660.

Example Horseshoe with Cuff-Attachment System

Figure 13:
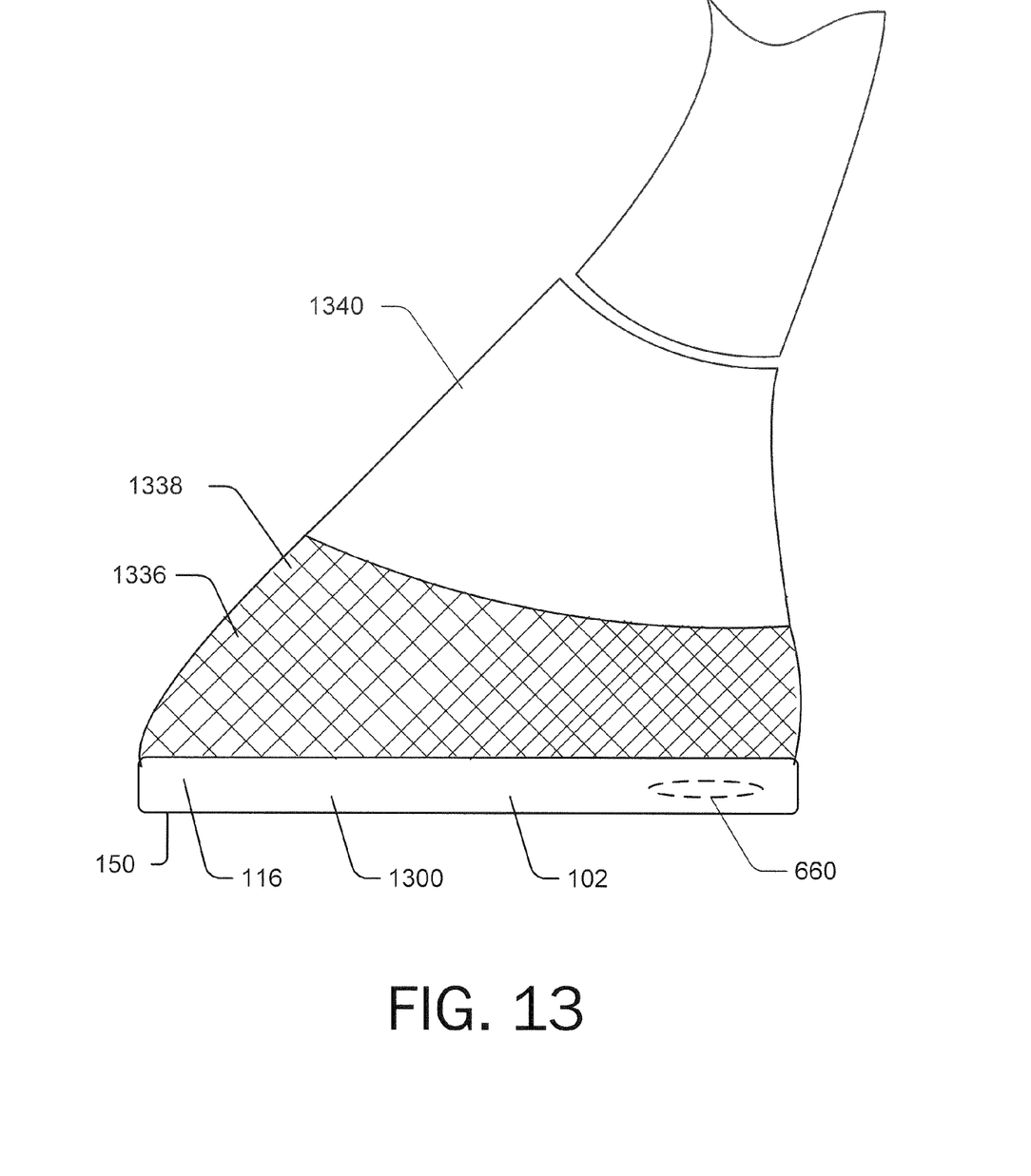
FIG. 13 shows an example horseshoe indirectly attached to horse's hoof using a fabric cuff.

FIG. 13 shows an example horseshoe 1300 (representing any of the aforementioned example horseshoes such as 100, 300, 400, 600, 1200) indirectly attached to horse's hoof using a fabric cuff 1336.

Cuff 1336 is generally secured (i.e., attached) within a portion of body 102. In one example, cuff 1336 is incorporated underneath an upper-most portion hoof-facing surface 110 (see e.g., FIGS. 1 and 2), and more specifically rim 117 (see e.g., FIGS. 1 and 2). That is, cuff 1336 is partly encapsulated within body 102. Additional details of how cuff 1336 is encapsulated in body 102 are discussed in U.S. Pat. No. 5,330,008, to Sigafoos et al. as well as U.S. Pat. No. 5,699,861 to Sigafoos, and U.S. Pat. No. 5,638,905 to Sigafoos et al., all incorporated fully herein by reference and will not be discussed further. Typically, cuff 1336 extends from outer edge 116 of shoe 1300.

In one example, cuff 1336 is a fabric configured to conform to a wall 1338 of a horse's hoof 1340 and attach thereto through the use of an adhesive. Cuff 1336 may include several layers of fabric material. Cuff 1336 may be used as a single ply or multi-ply layers. Each layer of material may be braided.

For example, in one implementation, cuff 1336 is constructed of roughly equal quantities of polyester and Vectran™ (a liquid crystal polymer of polyester) graded in a two-ply configuration. Polyester is used to deliver high bonding strength with adhesive, is flexible, and works well in wet environments without structural weakening. However, other suitable materials may be selected in place of polyester, which provide similar attributes as polyester as would be appreciated by those skilled with the benefit of having this disclosure, such as nylon, and other synthetic or non-synthetic materials.

A second potential component of the braid. Vectran™, is used to provide abrasion resistance for cuff 1336. The abrasion resistant material is incorporated to reduce and minimize the wear of the fabric due to contact with ground materials that a horse's hoof normally encounters, such as dirt, sand, gravel, etc. Other suitable abrasion resistant materials could be selected as would be appreciated by those skilled in the art having the benefit of this disclosure. For example, Dyneema® or Spectra® (high molecular weight polyethylene) or the like material could also be used as one of the ply material in place of, or in conjunction with, one of the plies. Thus, cuff 1336 may be constructed of strong and resistant material(s) able to undergo severe wear conditions.

Another aspect of cuff 1336 is its ability to contact hoof wall 1338. Horse's hooves are not uniform nor are the ground contact angles uniform from hoof to hoof. As a result of this factor, braided fabric may be used to shoe 1300 to a horse's hoof, because braided fabric is able to be contoured and shaped so that no wrinkles or folds occur when tightly bonding the cuff to the hoof wall.

In one implementation this feature is achieved through the use of a type of braid used where the fibers are aligned at angles other than the typical 90° found in many woven fabrics. For instance, an angle of approximately between 30° and 50° has the added benefit of positioning the fibers on the hoof in a way that utilizes all of the fibers in holding a shoe onto the hoof, and supporting the hoof wall radially as with hoop stress.

Other angles greater than 50° or less than 30° could be selected as well, but the least wrinkle free results were observed generally between 30° and 50°.

Thus, cuff 1336 reinforces a hoof wall 1338 and provides many benefits to a horse. For example, when implemented as fabric, cuff 1336 bridges and stabilizes cracks in the hoof wall. It may also cover and rebuild a broken section of the hoof, support a thin, weak or shelly hoof wall and, also help to uniformly distribute load on the entire hoof wall. Additionally, using multiple layers of adhesive saturated fabric acts as a durable cover protecting the hoof from damage due to work in an on various surfaces the animal lives, works, and performs upon.

Typically, most adhesives such as methacrylate or other acrylic adhesive may be used for attaching cuff 1336 to a horse's hoof. Please see U.S. Pat. No. 5,330,008, for a more detailed process of attaching cuff 1336 to a horse's hoof. As depicted in FIG. 13, example plate 660 is elliptical in shape, but as described above may be other shapes or configurations including the planar-rectangular examples described and illustrated above.

Body 102 of the example horseshoes describe above, may also include holes (not shown) for receiving nails, in the event there is a desire to fully or partially nail the elastomeric shoe to a horse's hoof. Such a shoe may offer the farrier the choice of selecting an all in one shoe (i.e., a glue-on or nail-on shoe).

Wear and Radiopaque Qualities

Figure 14:
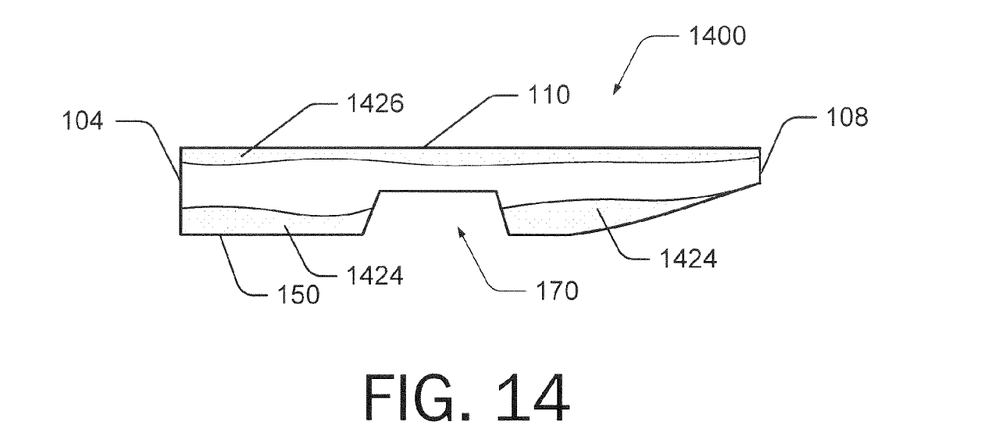
FIGS. 14 and 15 show cross-sectional views of a portion of an elastomeric shoe with wear and radiopaque materials therein.

FIG. 14 shows a cross-sectional view of a toe portion 104 of another elastomer horseshoe 1400. In the example horseshoe depicted in FIG. 14, there is no concave-relief section. Instead, hoof-facing surface 110 is generally planar. Like. FIG. 1B, horseshoe 1400 may include one or more nail creases 170 located along a portion of ground surface 150.

The body of a horseshoe may also include a wear material. For instance, wear material may be encapsulated in a horseshoe, and stratified toward ground-facing surface 150. Wear material may also be encapsulated evenly throughout a body of an elastomeric horseshoe. That is, in another aspect, the wear material may be dispersed uniformly throughout the entire horseshoe.

In addition, when a horseshoe is new and unworn, the ground-facing surfacing may initially include a thin layer of elastomeric material that does not include a wear-layer material. The thin layer of material may quickly rub off after the shoes are in use by a horse, thereby revealing the wear-layer material as part of the ground-facing surface.

In the example illustration of FIG. 14, wear-layer material 1424 is stratified toward ground-facing surfacing 150 of horseshoe 1400. Wear-layer material 1424 may include one or more suitable materials used to increase friction and/or durability of the bottom surface of any elastomeric shoe, such as the horseshoes illustrated in this disclosure. Example wear material may include titanium, carborundum, aluminum oxide, other suitable hard-wearing-particulate materials, or any combination of the foregoing.

Wear materials also act to improve the effective coefficient of surface friction of the primary elastomeric materials used in a horseshoe. Wear material 1424 is especially useful in grass or wet conditions. The use of a wear material 1424 that includes abrasive grit for grip and wear is in addition to any of a wide variety of ground surface patterns that can be used on a metal or "plastic" non-metallic horseshoe. Starting with a smooth bottom and proceeding thru the almost infinite variety of patterns that have been demonstrated by many generations of farriers and blacksmiths in an effort to improve traction on both metal and non-metallic horseshoes.

The typical "crease" or "fullering" on the ground surface of the shoe is generally understood to be where the nails are located and seated, is also important to traction as it tends to fill with stones and dirt while in use. These grit materials will complement traction when used with elastomeric shoes with a "crease".

The amount of wear material added to a shoe may range from percentages as low as 0.5% by weight of the entire shoe, and as high as 40% by weight. Although, as appreciated by those skilled in the art after having the benefit of this disclosure, a suitable percentage of wear material is typically a function of the specific abrasive material used, and the required performance properties of urethane or other materials comprising a horseshoe. That is, the suitable percentage is generally based on the physical characteristics of the specific elastomeric shoe, and abrasive materials used to make the horseshoe. For instance, too much abrasive material can degrade physical properties of a urethane shoe to the point where it affects the functional performance of the horseshoe.

Also, many elastomeric materials are transparent (i.e., radiolucent) to X-rays with X-rays commonly being used as a diagnostic tool employed by veterinarians in assessing hoof and leg problems. This elastomeric translucency to X-rays can be problematic, because the elastomeric materials may prevent the veterinarian from identifying the bottom-most portion of the hoof when the hoof is shod with an elastomeric shoe. Consequently, it is often necessary for the veterinarian to remove an otherwise satisfactory shoe.

Accordingly, in one example, one or more radiopaque materials may be added to the elastomeric horseshoe so that a veterinarian or radiologist is able to easily identify the margin where the hoof-shoe interface (i.e., hoof-facing surface 110) is located, without removing the shoes. That is, a radiopaque material may be stratified within, encapsulated in or over a horseshoe, sprayed-on, or layered-on a horseshoe.

For instance, in the example horseshoe 1400 depicted in FIG. 14, radiopaque material 1426 is stratified toward hoof-facing surface 110. The thickness of the radiopaque material 1426 may vary, but a suitable thickness is one that allows a radiologist or veterinarian to discern (i.e., see) the demarcation line between the hoof and shoe. For instance, in one example a thickness of a ¼ of ⅛$^{th}$ of an inch may be sufficient.

In another example, each horseshoe may be dipped in a liquid containing the radiopaque material 1426. This is sometimes referred to as dip molding.

Figure 15:
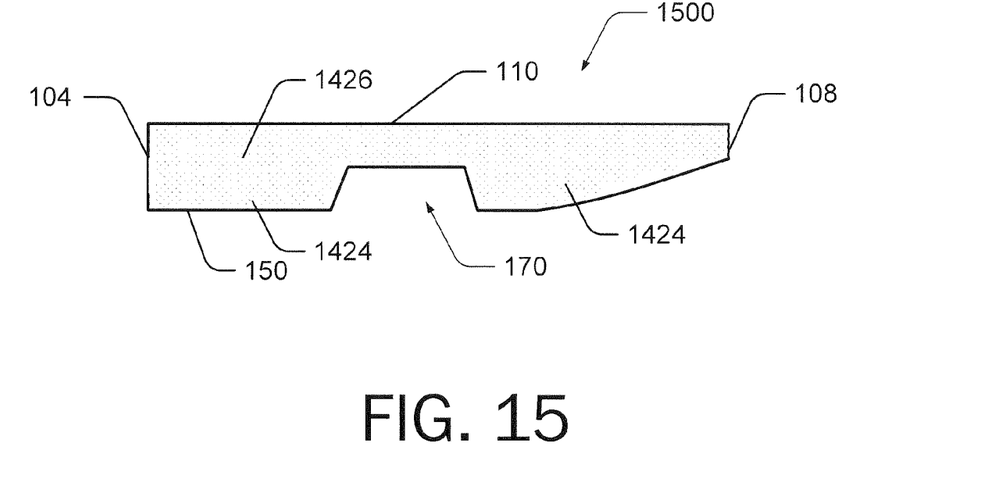

Still, in another example, radiopaque material 1426 may be mixed and dispersed uniformly throughout portions or all of the body of a horseshoe. In addition, radiopaque material 1426 may be intermixed with wear material 1424 and dispersed throughout most, if not all the body of a horseshoe such as illustrated in FIG. 15.

Further the same materials may be used for the radiopaque material 1426 and wear material(s) 1424. That is, it is possible to use one material to act as both a radiopaque material 1426 and wear material 1424. So, in some examples, the radio-opaque material can be combined with the wear material and/or can replace the need for a separate wear material.

As to the specific radiopaque materials, there are a variety of different types that may be used. For instance, in one example, a barium powder may be mixed into the elastomeric material. In another example, barium sulfate ($BaSO_4$) may be used. Other suitable materials may include. Bismuth, tungsten, or other metal powders mixed into the plastic shoe. With elastomers it is also possible to blend any of these radiopaque materials, as should be appreciated by those skilled in the art after having the benefit of this disclosure.

Further, these wear and radiopaque materials may be used in any elastomeric horseshoe, and are not limited to the example shoes and configurations described in this application. For instance, the wear and radiopaque materials may be used with elastomeric shoes that do not include braces and plates, etc.

In one aspect, the process for adding an abrasive-grit material (i.e., wear material) to urethane horseshoes may include the following steps:

1. Heat a pre-polymer to prepare for the process and vacuum degas the batch.

2. Mix appropriate weight of abrasive grit into a pre-measured quantity of pre-polymer . . . this will be added at the appropriate time to the final batch to be used in molding 3. Vacuum degas the mixed batch with the grit.

4. Add cross-linker to the urethane pre-polymer batch (no grit). The cross linker is an adequate quantity for the total weight of the final batch (including the grit portion).

5. Grit containing batch is added to the final total mix at a specific time during but before completion of the cross-linker addition.

a. In one aspect, a grit addition is a controlled weight ratio of approximately 2-to-18% of the total batch weight based on the specific product performance requirements of the shoe. Of course, as appreciated by those skilled in the art, the ratio ranges may be greater or less than 2-18%.

6. The grit/pre-polymer, cross-linked mixture is added to the pre-heated mold via a specialized mixing/pouring container which decants the mixture from the bottom of container.

7. By adjusting process reaction speed with catalysts and controlling the temperature profile, the grit settling rate toward the bottom of the mold can be regulated. By adjusting the reaction and temperature profiles, the grit can be uniformly distributed or stratified at predictable, modifiable levels within the horseshoe.

With respect to radio-opacity in an elastomeric horseshoe, the manufacturing process may be essentially the same as with the wear material mentioned above, but a radio-opaque material (e.g. Barium Sulfate) is used instead of or in addition to abrasive grit (i.e., wear material). The addition of the radio-opaque material is at a mix ratio (by weight) of approximately between 0.5% and 5% in order to achieve adequate visual separation between the horseshoe, and the hoof in the X-ray image. Of course, as appreciated by those skilled in the art, greater or lesser percentages of weight may be used depending on the material composition among other potential factors. Unlike the abrasive grit application the Barium Sulfate is a lighter, powder-like material and the dispersion of this additive in the urethane will tend to be uniform.

Conclusion

It is to be understood that the present invention is not limited to the embodiments described above, but encompasses any and all embodiments within the scope of the subjoined Claims and their equivalents.

What is claimed is:

1. A horseshoe, comprising: an elastomeric body having a ground-facing surface and a generally parallel hoof-facing surface opposite the ground-facing surface, wherein the body further includes a wear material between the ground-facing surface and the hoof-facing surface, wherein the wear material is an abrasive grit stratified in higher concentration toward the ground-facing surface, and in less concentration toward the hoof-facing surface, wherein the wear material is comprised substantially of aluminum oxide.

2. The horseshoe of claim 1, wherein the wear material forms, at least partially, the ground-facing surface, and comprises between about 2% and 18% by weight of the horseshoe.

3. The horseshoe of claim 2, wherein the radiopaque material, is encapsulated within the body of the horseshoe.

4. The horseshoe of claim 1, further comprising: a radiopaque material sandwiched between the hoof-facing surface and the ground-facing surface, wherein the radiopaque material includes at least one of barium, barium sulfate (BaSO4), Bismuth, tungsten, and a blend of metal powder and plastic.

5. The horseshoe of claim 4, wherein the radiopaque material forms, at least partially, the hoof-facing surface of the horseshoe.

6. The horseshoe of claim 4, wherein the radiopaque material is stratified in higher concentration toward the hoof-facing surface, and in less concentration approaching the ground-facing surface.

7. The horseshoe of claim 4, wherein the body includes a mixture of the radiopaque material and the wear material.

8. The horseshoe of claim 1, wherein the wear material is encapsulated within the body of the horseshoe.

* * * * *